United States Patent
Reichmann (10) Patent No.: US 10,195,310 B2
(45) Date of Patent: Feb. 5, 2019

(54) DEVICE AND METHOD FOR COMPRESSING A HYDROGEL

(71) Applicant: UNIVERSITÄT ZÜRICH, Zürich (CH)

(72) Inventor: Ernst Reichmann, Adligenswil (CH)

(73) Assignee: UNIVERSITÄT ZÜRICH, Zürich (CH)

( * ) Notice: Subject to any disclaimer, the term of this patent is extended or adjusted under 35 U.S.C. 154(b) by 199 days.

(21) Appl. No.: 14/901,108

(22) PCT Filed: Jun. 27, 2014

(86) PCT No.: PCT/EP2014/063786
§ 371 (c)(1),
(2) Date: Dec. 28, 2015

(87) PCT Pub. No.: WO2014/207251
PCT Pub. Date: Dec. 31, 2014

(65) Prior Publication Data
US 2016/0136333 A1    May 19, 2016

(30) Foreign Application Priority Data

Jun. 28, 2013 (EP) .................. 13174441

(51) Int. Cl.
*A61L 27/60* (2006.01)
*A61L 27/38* (2006.01)
(Continued)

(52) U.S. Cl.
CPC ........... *A61L 27/60* (2013.01); *A61L 27/3804* (2013.01); *A61L 27/3813* (2013.01); *A61L 27/52* (2013.01);
(Continued)

(58) Field of Classification Search
CPC ............ H04L 61/2007; H04L 61/2084; H04L 61/2514; H04L 61/6068; H04W 36/0016;
(Continued)

(56) References Cited

U.S. PATENT DOCUMENTS

2012/0288911 A1   11/2012   Matos
2013/0099407 A1    4/2013   Tully

FOREIGN PATENT DOCUMENTS

CN       101421388 A      4/2009
JP       2002-510482      4/2002
WO       20120004564      1/2012

OTHER PUBLICATIONS

Diezi, Mirco, "Determining the conditions that regulate epidermal stratification in vitro: Engineering an epidermal substitute in 3 steps", Master Thesis in Human Biology, Tissue Biology Research Unit, University of Zürich, Feb. 2009.
(Continued)

*Primary Examiner* — Gautam Prakash
*Assistant Examiner* — Lydia Edwards
(74) *Attorney, Agent, or Firm* — Soroker Agmon Nordman (57) ABSTRACT

The invention relates to a device and a method for compressing a hydrogel layer (H), wherein a separate piston (600) that is designed to be connected to a second component (400) of the device in a releasable manner in an operating mode of the device, particularly by means of a latching connection, presses along a compression direction (C) against said hydrogel layer (H) residing on a membrane bottom (501) of a graft frame (500) so as to compress the hydrogel layer (H) between the piston (600) and the membrane bottom (501).

16 Claims, 11 Drawing Sheets

(51) Int. Cl.
  *A61L 27/52*  (2006.01)
  *C12M 1/24*  (2006.01)
  *C12M 1/00*  (2006.01)
  *C12M 3/00*  (2006.01)
  *C12M 1/12*  (2006.01)
  *C12N 5/071*  (2010.01)
  *A61F 2/10*  (2006.01)

(52) U.S. Cl.
  CPC ............ *C12M 23/08* (2013.01); *C12M 23/22* (2013.01); *C12M 23/48* (2013.01); *C12M 25/14* (2013.01); *C12M 25/18* (2013.01); *C12N 5/0629* (2013.01); *A61F 2/105* (2013.01); *A61L 2430/34* (2013.01); *C12N 2533/90* (2013.01); *C12N 2537/00* (2013.01)

(58) Field of Classification Search
  CPC .... H04W 36/12; A61F 2/105; A61L 2430/34; A61L 27/3804; A61L 27/3813; A61L 27/52; A61L 27/60; C12M 23/08; C12M 23/22; C12M 23/48; C12M 25/14; C12M 25/18; C12N 2533/90; C12N 2537/00; C12N 5/0629
  See application file for complete search history.

(56) References Cited

OTHER PUBLICATIONS

Baroli, B., "Hydrogels for tissue engineering and delivery of tissue-inducing substances", J Pharm Sci, (2007), vol. 96, No. 9, pp. 2197-2223.

Mimura, T. et al., "Tissue engineering of corneal stroma with rabbit fibroblast precursors and gelatin hydrogels", Mol Vis, (2008), vol. 14, pp. 1819-1828.

Stark, H.J. et al., "Organotypic keratinocyte cocultures in defined medium with regular epidermal morphogenesis and differentiation", Journal of Investigative Dermatology, (1999), vol. 112, No. 5, pp. 681-691.

Yamaoka, H. et al., "Cartilage tissue engineering using human auricular chondrocytes embedded in different hydrogel materials", J Biomed Mater Res A, (2006), vol. 78, No. 1, pp. 1-11.

DEVICE AND METHOD FOR COMPRESSING A HYDROGEL

RELATED APPLICATIONS

The present application claims priority as a US national phase under 35 U.S.C. 363 of PCT/EP2014/063786 filed on Jun. 27, 2014, the disclosure of which is incorporated herein by reference.

SPECIFICATION

The present invention relates to a device for compressing a hydrogel according to claim 1 as well as to a method for compressing such a hydrogel according to claim 15 as well as to systems according to claims 13 and 14.

In the human body, cells usually reside in a three-dimensional (3D) macromolecular network, the so-called ECM. In order to mimic the 3D-environment in cell culture, hydrogels can be used.

In this regard, a hydrogel is a network of natural or synthetic, particularly water insoluble, polymer chains able to absorb particularly over 99% of water. The hydrophilicity of the network originates from the existence of chemical residues present within the polymer backbone or lateral chains [1, 2].

With their biocompatibility and flexibility, similar to natural tissue, hydrogels are predestined for applications in the field of tissue engineering of cornea [3], skin [4], cartilage [5], tendon [6] or vascular tissue. Another main advantage of hydrogels is the possibility to integrate easily living cells within a 3-D matrix. To produce a dermo-epidermal skin substitute, dermal fibroblasts are to be submerged within the collagen type I hydrogel, which "traps" these cells upon gelification in three dimensions. Collagen type I provides a natural matrix for these cells and ideally supports their proliferation, migration and differentiation. Importantly, these fibroblasts provide necessary factors (within six days), and hence the supporting micro-environment for the keratinocytes to be added on the plane upper surface of the hydrogel, 6 days after the gel (containing the fibroblasts) was prepared.

Since the hydrogel has a flabby consistence, it is necessary to plastically compress it, so as to improve its biological properties, but also to increase its physical robustness, which then allows the surgeon to conveniently and securely handle the final gel/skin graft made from the compressed hydrogel.

Therefore, based on the above, the problem underlying the present invention is to provide a device, a system as well as a method for compressing such a hydrogel. This problem is solved by a device having the features of claim 1 as well as a method having the features of claim 15 as well as by systems having the features of claims 13 and 14.

According to claim 1, the device according to the invention comprises: a separate graft frame comprising a circumferential frame member and a permeable membrane bottom connected to said frame member, wherein the graft frame is designed to receive said hydrogel so that a hydrogel layer is formed (i.e. the hydrogel in the graft frame extends along the membrane bottom, wherein its dimensions along the membrane bottom are larger than the thickness of the hydrogel perpendicular to the membrane bottom) covering said membrane bottom; a guiding frame having a plurality of guiding rods extending along a compression direction; a filter plate; a first (e.g. lower) component comprising a base having a plurality of openings, particularly formed in an outer edge region of said base, wherein each opening is associated to one of the guiding rods, wherein the first component is designed to be arranged on the guiding frame in an operating mode of the device such that each guiding rod extends through its associated opening, wherein the first component further comprises a circumferential wall protruding from the base of the first component, so that the first component forms a container that is designed to receive the filter plate and the graft frame in said operating mode so that the filter plate is arranged between a bottom of said container of the first component and the membrane bottom of the graft frame; a second (e.g. upper) component comprising a base having a plurality of openings, particularly formed in an outer edge region of said base of the second component, wherein each opening is associated to one of the guiding rods, wherein the second component is designed to be arranged on said first component in said operating mode, such that each guiding rod that extends through its associated opening of the first component is also inserted into its associated opening of the second component so that the second component is slideably guided by said rods along the compression direction; a separate piston that is designed to be connected to said second component in a releasable manner in said operating mode of the device, particularly by means of a latching connection, wherein in said operating mode of the device the second component is designed to press the piston along the compression direction against said hydrogel layer residing on the membrane bottom of the graft frame so as to compress the hydrogel layer between the piston and the membrane bottom.

Preferably, such a hydrogel layer is used for generating an artificial skin graft that can be implanted onto a patient.

Preferably, the hydrogel consists of medical grade bovine collagen type I. Particularly, human autologous dermal fibroblasts are contained in the hydrogel, and human autologous keratinocytes are situated on the hydrogel, i.e., at an upper surface of the hydrogel layer facing away from said membrane bottom, on which the hydrogel resides. Said membrane or membrane bottom is permeable for water that is squeezed out of the layer during compression as well as for cell culture medium, so that the latter can reach the hydrogel from both underneath and above.

Preferably, the membrane bottom preferably consists of PET, is preferably 18 micrometers thick and microporous, with a pore-diameter of preferably 3 micrometers.

According to a preferred embodiment of the present invention, the graft frame and/or the piston are designed as single-use items (i.e. are designed to be replaced after a single use). Thus, there is no need for autoclaving these items every time before using them.

Further, according to a preferred embodiment of the present invention, the piston comprises an e.g. plate-like piston base having a first side forming a contact surface for pressing against the hydrogel layer. Preferably, the piston is designed to be inserted into the graft frame with said contact surface ahead when pressing with its contact surface against the hydrogel layer. Furthermore, particularly, the piston base comprises a circumferential edge region being designed to contact the frame member of the graft frame when pressing against the hydrogel layer, so as to prevent hydrogel from flowing out of the graft frame through a gap between the piston and the frame member upon compressing the hydrogel layer.

According to a further preferred embodiment of the present invention, the piston comprises two latching elements, particularly protruding from said edge region of the piston base on a second side of the piston base facing away from said first side forming said contact surface. This allows for an easy manual fastening of the piston to the second component as well as releasing the piston from the second component by manually disengaging it with the second component.

Preferably, the second component comprises a support for holding the piston, which support protrudes from a first side of the base of the second component towards the membrane bottom in said operating mode of the device. Preferably, said latching elements are designed to engage with said support for releasably connecting the piston to the support.

Further, according to a preferred embodiment of the present invention, the base of the second component comprises an aperture for each latching element, through which the respective element is accessible, e.g. manually or by means of a tool, from a second side of the base of the second component facing away from said first side of the base, so that the latching elements can be released from the support through said apertures, for instance by bending them away from the support in order to bring them out of engagement with the support.

Further, according to a preferred embodiment of the present invention, the piston comprises guiding elements protruding from said edge region of the piston base on said second side of the piston base facing away from said contact surface, wherein said guiding elements are designed to slide along said support for guiding the piston with respect to the support when the piston is connected to the support.

Furthermore, according to a preferred embodiment of the present invention, the second component comprises an adjusting means for adjusting a penetration depth of the piston along the compression direction into the graft frame, i.e., for adjusting the thickness of the hydrogel layer after compression, wherein particularly said adjusting means comprises two screws that are screwed in an internal thread formed in the first side of the base adjacent to the support so that the heights of the screw heads of said screws with respect to said first side the base can be adjusted by turning the respective screw clockwise or counterclockwise. Preferably, the screw heads are designed to butt against said frame member in the operating mode of the device so as to limit said penetration depth. Preferably, each screw is arranged adjacent to a corner region of the support, wherein said corner region of the support face each other diagonally.

Further, according to a preferred embodiment of the present invention, the base of the second component comprises a receptacle for receiving at least one weight, preferably a plurality of weights, so as to adjust the weight of the second component, by means of which the second component compresses said hydrogel layer in said operating mode of the device, wherein particularly said receptacle is formed by said support. Preferably, said receptacle comprises an opening on the second side of the base of the second component, through which opening said at least one weight or said plurality of weights can be arranged in said receptacle.

Preferably, for supporting said filter plate, the circumferential wall of the container preferably comprises a step on which the filter plate can rest with an edge region of the filter plate.

Furthermore, said graft frame is preferably designed to rest with a circumferential edge region of the frame member on an upper edge of the wall of the container in said operating mode of the device. In order to further stabilize the position of the graft frame within the container, said upper edge of the wall preferably comprises at least one recess for receiving a region of the frame member in a form-fitting manner.

Further, in order to be able to remove the graft frame and/or said filter plate easily from the container of the first component, said wall of the container preferably comprises a bulge for taking the filter plate and/or the graft frame out of the container. Preferably, said bulge is formed such that a finger of a user or the tip of a suitable tool can be inserted into the interior region of the container delimited by said bulge so that the graft frame and/or filter plate can be lifted and removed from the container by means of a finger or said tip of a tool.

Further, according to another aspect of the present invention a system according to claim 13 is provided, comprising a device according to the invention as well as a flask for incubation of the compressed hydrogel layer. Preferably, said flask is designed to receive the graft frame with the compressed hydrogel layer residing in said graft frame. For this, the flask preferably comprises an opening through which the graft frame can be arranged in an interior of the flask. Furthermore, said flask comprises a support frame being designed to be arranged in said interior of the flask on a bottom of the flask and to support the graft frame. For closing said opening properly, a lid of the flask is preferably provided, which is particularly designed to press the graft frame against the support frame when the lid closes said opening of the flask (there may also be an additional separate element being designed to be arranged between the graft frame and the lid, wherein the lid presses against this element and the element in turn presses against the graft frame which is then pressed against the support frame when the lid closes said opening).Further, the flask may comprise a further opening for filling in, or sucking off a cell culture medium or cells under routine cell culture conditions, wherein particularly a screw cap is provided for closing said further opening. For better inspection of the hydrogel (or cells), the flask is preferably designed transparent. Finally, said flask as well as said support frame is preferably designed as a single-use item.

Further, according to another aspect of the present invention, a graft frame according to claim 14 is provided. According thereto the graft frame comprises a circumferential frame member and a membrane bottom (see e.g. also above) connected to said frame member, wherein the graft frame is designed to receive a hydrogel so that a hydrogel layer is formed covering said membrane bottom (see e.g. also above).

Particularly, the membrane bottom is integrally connected to the frame member.

Particularly, the graft frame is designed as a single-use item (i.e. is designed to be replaced after a single use).

Particularly, the graft frame is designed to be inserted into a container of a device for compressing a hydrogel layer residing on the membrane bottom. Preferably, said device is the device according to the invention.

Further, particularly, said system according to claim 14 further comprises a flask for incubation of the compressed hydrogel layer residing in the graft frame on the membrane bottom.

Particularly, said flask is designed to receive the graft frame with the compressed hydrogel layer residing in said graft frame on the membrane bottom, i.e., advantageously the usage of the graft frame is twofold. At first, the graft frame serves for holding the hydrogel to be compressed, and thereafter as a means for holding the compressed hydrogel layer during incubation as well as transportation to the patient.

Particularly, the flask comprises an opening through which the graft frame can be arranged in an interior of the flask.

Particularly, the flask comprises a lid for closing said opening.

Particularly, said system according to claim 14 further comprises a separate support frame being designed to be arranged in said interior of the flask on a bottom of the flask and to support the graft frame.

Particularly, the lid is designed to press the graft frame against the support frame when the lid closes said opening of the flask (there may also be an additional separate element being designed to be arranged between the graft frame and the lid, wherein the lid presses against this element and the element in turn presses against the graft frame which is then pressed against the support frame when the lid closes said opening).

Particularly, the flask comprises a further opening for filling a liquid, particularly a cell culture medium, into the flask.

Further, particularly, a screw cap is provided for closing said further opening.

Further, particularly, said flask is transparent at least in sections.

Particularly, said flask and/or the support frame are designed as single-use items (i.e. are designed to be replaced after a single use). Furthermore, the problem according to the invention is solved by a method for compressing a hydrogel layer according to claim 15, particularly for generating an artificial skin graft, using a device according to the invention (eventually in combination with said flask), comprising the steps of: filling a hydrogel into the graft frame so that said hydrogel forms a layer covering said membrane bottom, particularly incubating the hydrogel layer in the graft frame, arranging the filter plate in said container of the first component, arranging said graft frame comprising the hydrogel layer in said container on top of the filter plate, arranging the first component on the guiding frame so that the guiding rods extend through their respective opening of the first component, arranging the second component on the first component so that said guiding rods are inserted into their respective opening of the second component, compressing the hydrogel layer between the membrane bottom and the piston connected to the second component by letting the second component press with the piston along the compression direction against the hydrogel layer, wherein the second component is guided by said guiding rods along the compression direction, and particularly removing the graft frame from the device after having compressed the hydrogel layer, particularly arranging the graft frame with the compressed hydrogel layer through an opening of a flask into an interior of the flask on top of a support frame arranged on a bottom of the flask, particularly closing the flask with a lid, thereby pressing the frame member of the graft frame with the lid against the support frame so as to secure the graft frame in the flask, and particularly incubating the compressed hydrogel layer so as to generate an artificial skin graft from said compressed hydrogel layer.

According to an embodiment of the present invention, said hydrogel is generated as follows: Collagen type I can be purchased dissolved in an acidic solution. To gelify this collagen it has to be neutralized by a basic buffer. Subsequently complete gelification takes e.g. 120 minutes at e.g. 37° C. in a cell incubator. Thereafter the hydrogel can be compressed.

Further, after having compressed the hydrogel, the compressed hydrogel is preferably processed as follows: The compressed hydrogel containing the fibroblasts is incubated for e.g. 6 days until the fibroblasts have proliferated to biologically reasonable cell numbers. Thereafter keratinocytes are added to the plane upper surface of the gel. After additional e.g. 6 days (12 days in total) the keratinocytes have formed a stratified epithelium (the epidermis). Thus after 12 days the "hydrogel" which now has turned into a dermo-epidermal skin graft can be transplanted onto the patient.

Further features and advantages of the invention shall be described by means of detailed descriptions of an embodiment with reference to the Figures, wherein.

FIGS. 1 to 16 show a device for compressing a hydrogel H. The device comprises a guiding frame 100 being designed for holding/guiding a first and a second component 200, 400 of the device with respect to each other, so that the second component 400 can press with a piston 600 along a compression direction C against a hydrogel layer H arranged in a graft frame 500 positioned on the first component 200 in a guided manner.

Figure 1:
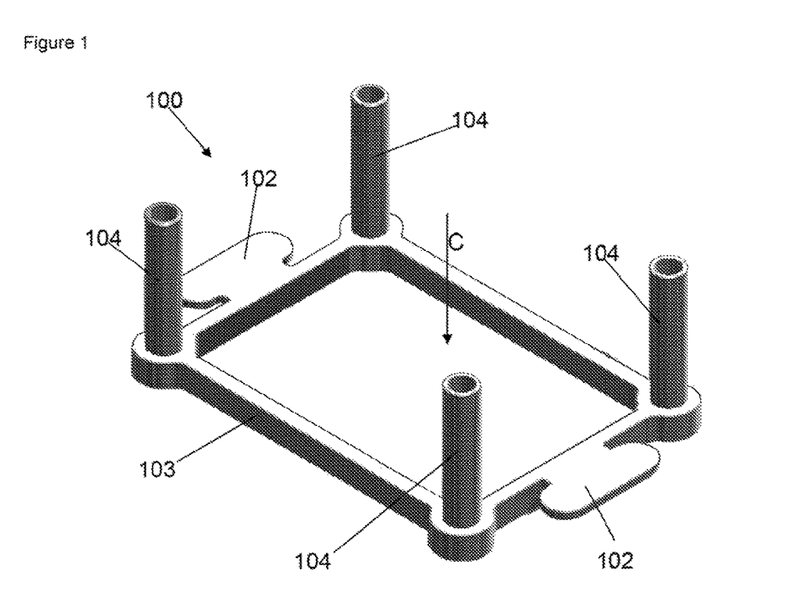
FIG. 1 shows a perspective view of a guiding frame of a device according to the invention.

As shown in FIG. 1 said guiding frame 100 comprises a rectangular frame member 103 formed out of four legs that are connected to each other in four corner regions of the frame member 103, wherein said frame member 103 extends or is positioned on an underlayment—when the device or guiding frame 100 resides in an operating mode—along a horizontal plane, and wherein from each corner region of the frame member 103 a guiding rod 104 protrudes from the frame member 103 counter to said compression direction C that is oriented perpendicular to said horizontal plane.

Figure 2:
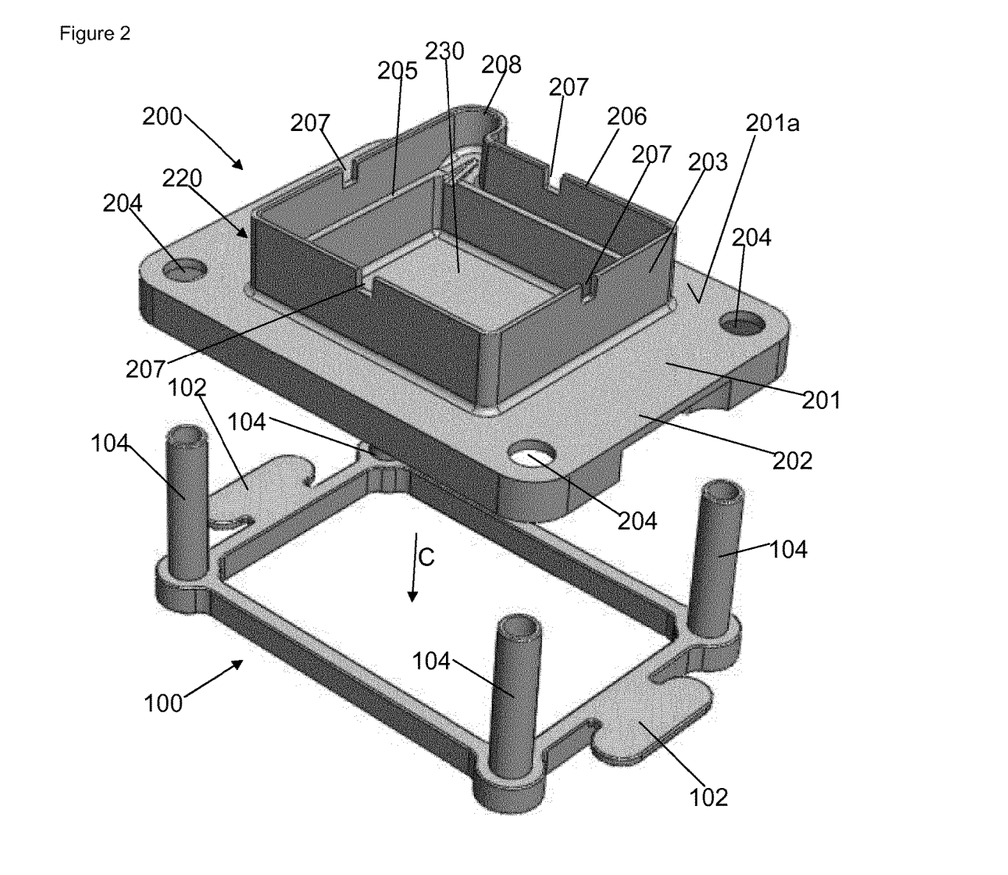
FIG. 2 shows a perspective view of the guiding frame shown in FIG. 1 as well as first lower component of the device according to the invention comprising a container for receiving a filter plate and a graft frame in which the hydrogel layer resides.
Figure 3:
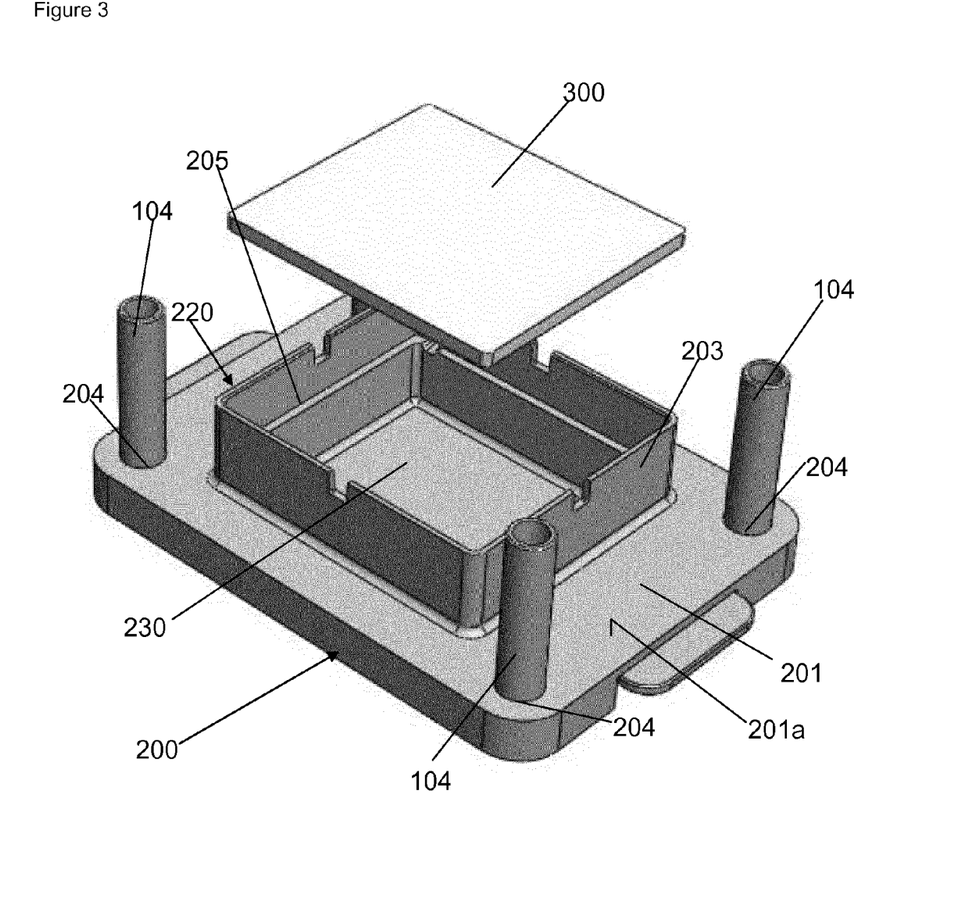
FIG. 3 shows a perspective view of the filter plate that is to be arranged in said container and the first component being arranged on the guiding frame.

As shown in FIG. 2 said first component 200 comprises a rectangular base 201 comprising a circumferential edge region 202 in which four openings 204 are formed, namely one in each corner region of the base 201 of the first component 200. Each opening is designed to receive one of the guiding rods 104 of the guiding frame, so that said guiding rods 104 extend through their respective opening 204 of the base 201 of the first component, when the first component is arranged on top of the guiding frame 100 as shown in FIG. 3. Further, as illustrated in FIG. 2, the guiding frame 100 comprises two handles 102 protruding from opposite legs of the frame member 103 of the guiding frame 100. These handles 102 serve for moving or carrying the guiding frame 100, particularly together with the first and the second component 200, 400 arranged thereon.

Figure 5:
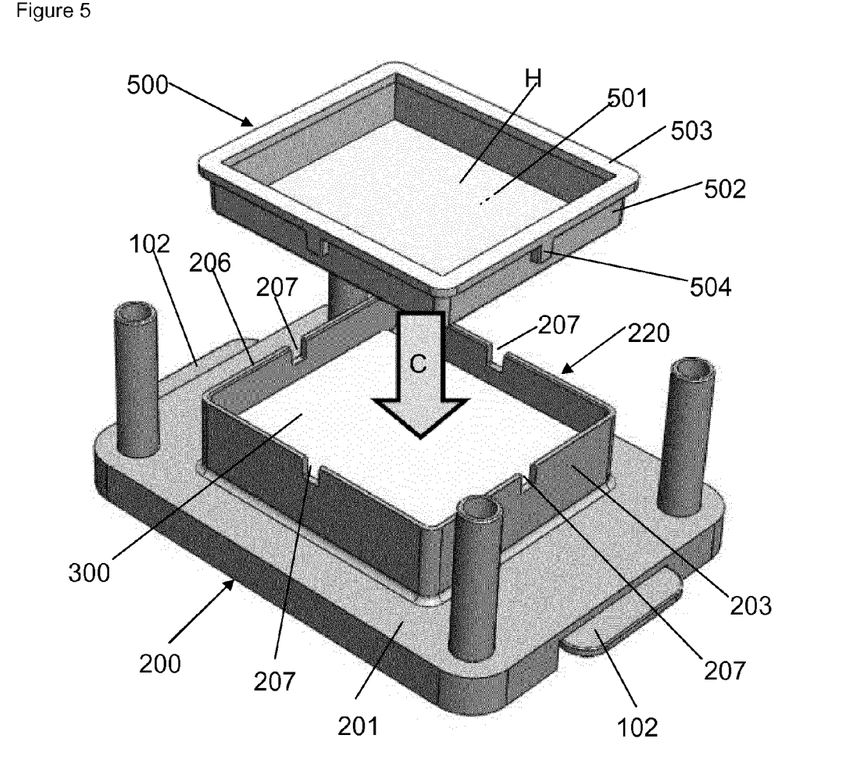
FIG. 5 shows a perspective view of the arrangement of the graft frame in said container on top of the filter plate.
Figure 6:
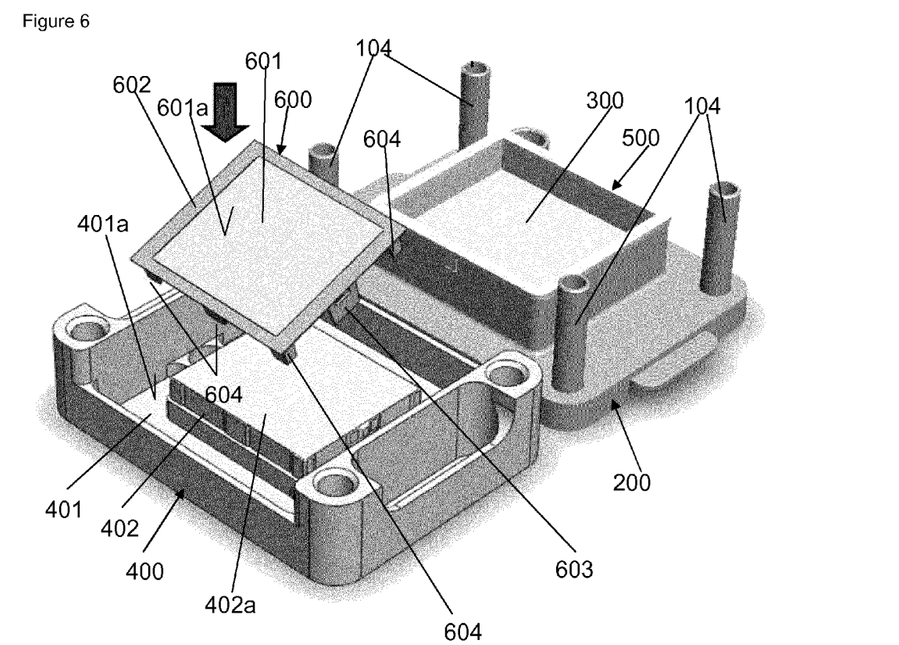
FIG. 6 shows the fastening of a piston to the second component as well as said first component holding the filter plate and the graft frame.
Figure 7:
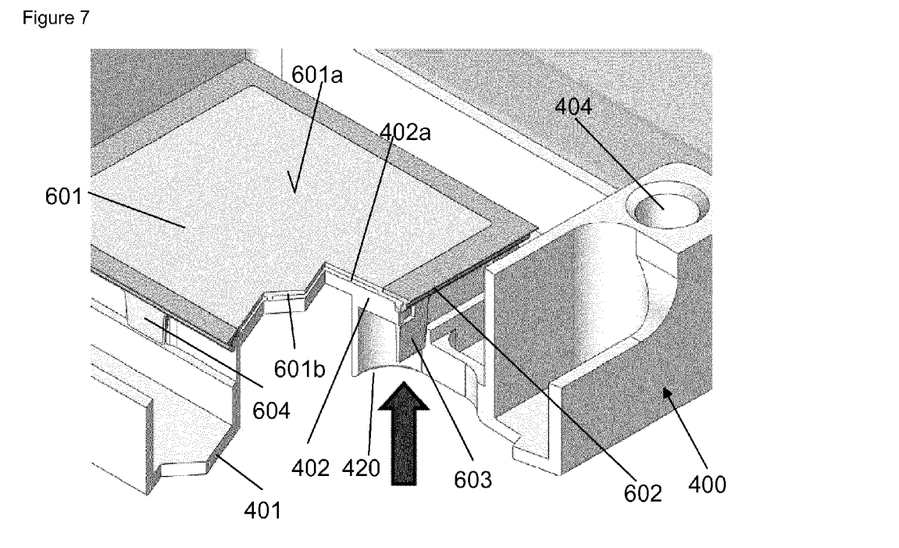
FIG. 7 shows a perspective view of a detail of the second component and the piston connected thereto.
Figure 8:
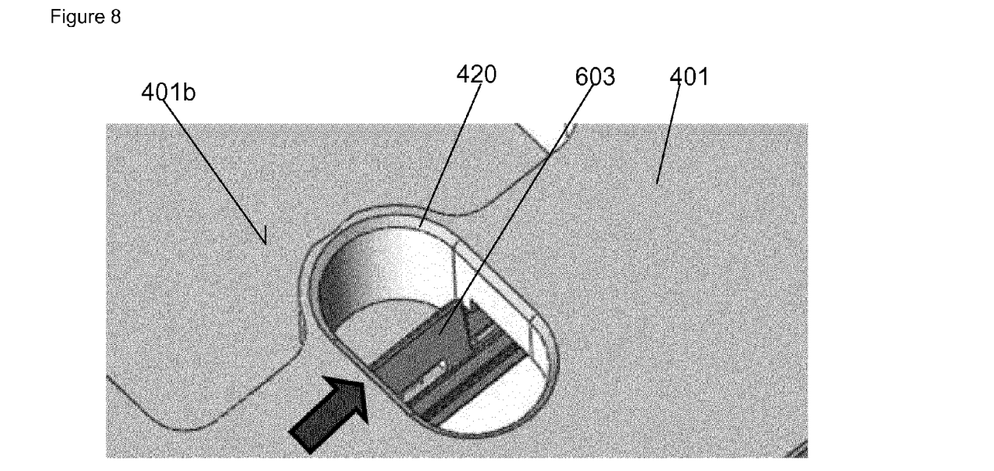
FIG. 8 shows a further perspective view of a detail of the second component.
Figure 9:
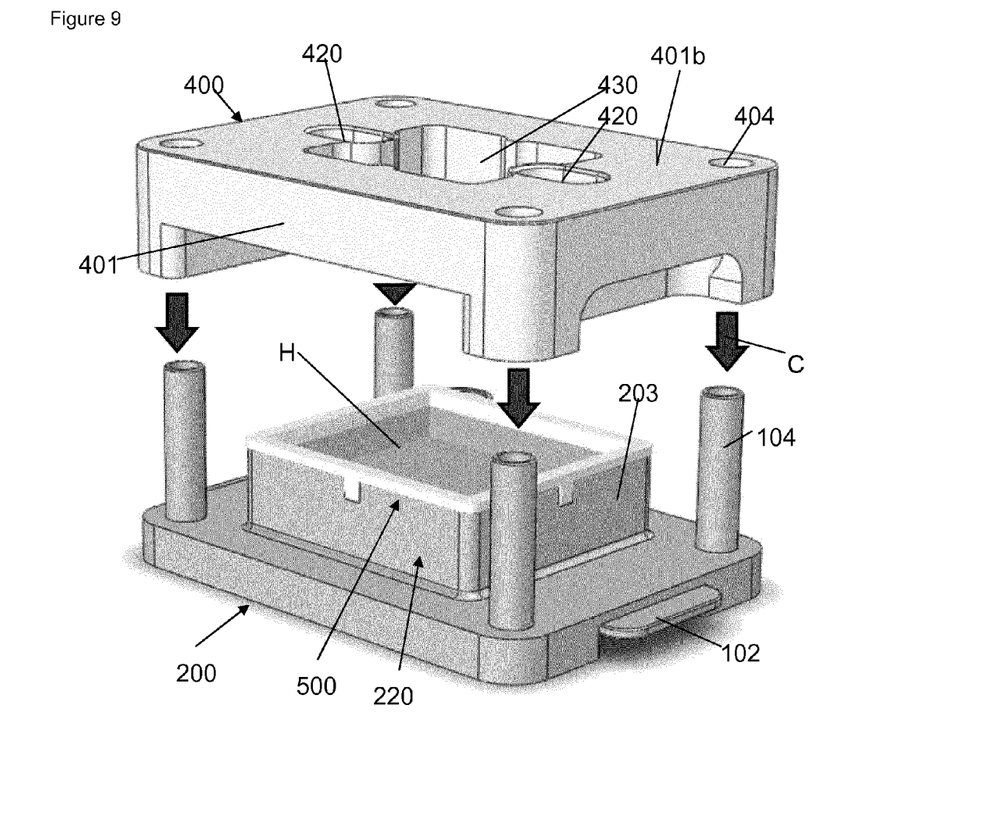
FIG. 9 shows a perspective view of the second component upon arrangement of the latter on the first component and on the guiding frame.

The base 201 of the first component 200 further comprises a first or upper side 201a from which a circumferential wall 203 protrudes so that a central portion of the base 201, e.g. a bottom 230, as well as said wall 203 form a container 220 for receiving a filter plate 300 and a graft frame 500 on top of the filter plate as indicated in FIGS. 3, 5 and 6.

The graft frame 500, which is e.g. shown in FIG. 5 comprises a circumferential (e.g. rectangular) frame member 502 and a membrane bottom 501 (i.e. a bottom forming a membrane) connected to said frame member 502, wherein the graft frame 500 is designed to receive a hydrogel so that a hydrogel layer H is formed covering said membrane bottom 501 The membrane preferably consists of PET, is 18 micrometers thick and microporous, with a pore-diameter of preferably 3 micrometers.

Advantageously, the graft frame with its membrane bottom 501 can be used for compressing the hydrogel as well as a carrier for holding the hydrogel after compression, e.g. during incubation. Advantageously, during incubation, a cell culture medium can reach the hydrogel layer from below (through the membrane bottom) as well as from above.

Further, the frame member 502 of the graft frame 500 comprises an upper circumferential edge region 503 as well as regions 504 protruding from each of the four legs of the frame member 502.

The filter plate 300 has a rectangular outer contour and is arranged such in the container 220 of the first component 200 that an outer circumferential edge of the filter plate rests on a step 205 of the wall 203 of the container 220 as shown in FIGS. 3 and 5. The graft frame 500 is placed on top of the filter plate 300 so that the membrane bottom 501 of the graft frame 500 rests on the filter plate 300, and such that the upper circumferential edge region 503 of the graft frame 500 rests on an upper edge 206 of the wall 203 of the graft frame, wherein said protruding regions 504 of the graft frame 500 engage with corresponding recesses 207 formed in said upper edge 206 of the wall 203 of the container 220 in a form-fitting manner.

Figure 10:
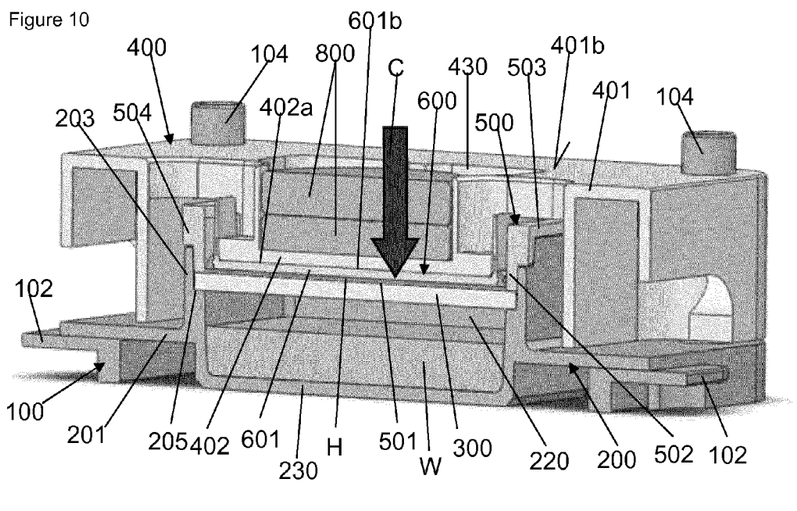
FIG. 10 shows a cross section of the device according to the invention in an operating mode.

Upon compression of the hydrogel layer H, which will be described below, excess water W is pressed through the membrane bottom 501 of the graft frame and flows through said filter plate 300 supporting the membrane bottom 501 into the container 220 where it accumulates on the bottom 230 of the container 220 as shown in FIG. 10, for instance.

In order to remove the graft frame as well as the filter plate from the container 220, the wall 203 of the container comprises a bulge 208 as shown in FIG. 2 that allows for manually removing the graft frame 500 as well as the filter plate 300 from the container 220, e.g., by means of a finger.

When the graft frame 500 is arranged in the container 220 as intended (cf. FIG. 6), the second component 400 is used to compress the hydrogel layer H along the compression direction C as shown in FIG. 10.

Figure 4:
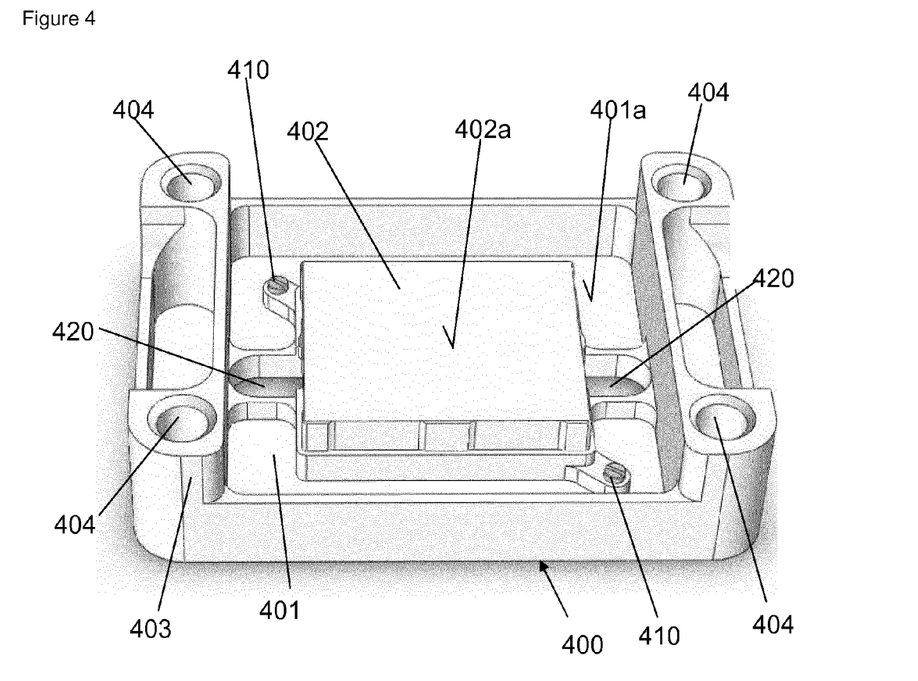
FIG. 4 shows a perspective view of a second upper component of the device according to the invention for compressing the hydrogel layer.

As illustrated in FIG. 4 the second component 400 comprises a base 401 comprising a circumferential edge region 403 in which four opening 404 are formed, i.e. one opening 404 in each corner region of the base 401 of the second component 400. Each of these openings 404 receives an associated guiding rod 104 when the second component 400 is arranged on the first component 200 (cf. FIG. 9) so that a movement of the second component 400 towards the first component 100 takes place precisely in the compression direction C.

Before arranging the second component 400 on the first component 200 a separate piston 600 is arranged on a support 402 of the second component 400 which protrudes from a first or lower side 401a of the base 401 of the second component 400 along the compression direction C, and which comprises a first or lower side 402a facing the hydrogel layer H in the operating mode of the device according to the invention, wherein said first side 402a extends perpendicular to the compression direction C.

The piston 600 comprises a plate-like (e.g. rectangular) piston base 601 having a first or lower side 601a extending perpendicular to the compression direction C, wherein said first side 601a forms a contact surface of the piston 600 for pressing against the hydrogel layer H as well as a circumferential edge region 602 for contacting the wall 203 of the container 220 from within in a sealing manner when the contact surface 601a presses against the hydrogel layer H, so that the hydrogel H stays inside the container 220 and cannot get past piston 600.

For connecting the piston 600 to the support 402 of the second component 400, the piston 600 comprises two latching elements 603 and a plurality of guiding elements 604 protruding from the circumferential edge region 602 as well as from a second side 601b of the piston base 601 facing away from said contact surface 601a, wherein said latching elements 603 are designed to engage with the support 402 to releasably fasten the piston 600 to the support 402, and wherein said guiding elements 604 are designed to guide the piston 600 with respect to the support 402 upon engaging the latching elements 603 with the support 402 (cf. FIG. 6). When the piston 600 is fastened to the support 402 by means of the latching elements 604 the second side 601b of the piston base 601 extends along or butts against the first side 402a of the support 402 (cf. FIGS. 7 and 10).

In order to adjust a penetration depth of the piston 600 into the graft frame 500, i.e., the thickness of the compressed hydrogel layer H, along the compression direction C, the second component comprises two screws shown in FIG. 4 that are strewn in an internal thread formed in the first side 401a of the base of the second component 400 adjacent to corner regions of the support 402, wherein said corner regions face each other diagonally.

Figure 11:
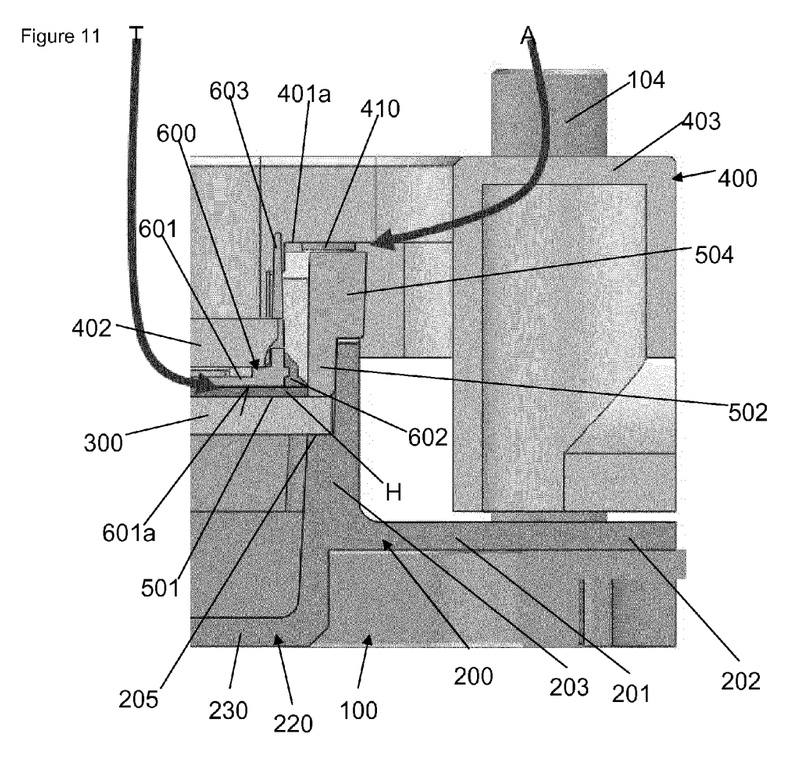
FIG. 11 shows a detail of the cross section shown in FIG. 10.

As can be seen from FIGS. 10 and 11, the screw heads of these screws 410 rest on the upper edge region 503 of the frame member 502 of the graft frame 500 (see position A in FIG. 11), when the contact surface 601 a of the piston 600 connected to the second component 400 presses under guidance of the guiding rods 104 against the hydrogel layer H residing on the membrane bottom 501 of the graft frame 500.

Thus, the more these screw heads protrude from the first side 401a of the base 401 of the second component, the thicker the compressed hydrogel layer H becomes (see position T in FIG. 11).

A force for compressing the hydrogel layer is provided by the weight of the second component and the parts attached thereto (e.g. the piston 600).

For adjusting said weight, the second component 400 comprises a receptacle 430 on a second side 401b of the base 401 facing away from said first side 401a, which receptacle 430 is formed or delimited by said support 402 for supporting the piston 600. Said receptacle 430 is designed to receive one or several weight elements 800 by means of which the overall weight of the second component 400 including the piston 600 can be adjusted (cf. FIGS. 9 and 10).

After having compressed the hydrogel layer H as intended by means of the device according to the invention, the second component 400 is removed from the first component 200 and the guiding frame 100. For this, the base 401 of the second component 400 comprises apertures 420 via which the latching elements 603 are accessible from the second side 401b of the basis, e.g. by means of a finger, so that said latching elements 603 can be brought out of their engagement with the support 402 of the second component 400 (cf. FIGS. 8 and 9).

Figure 12:
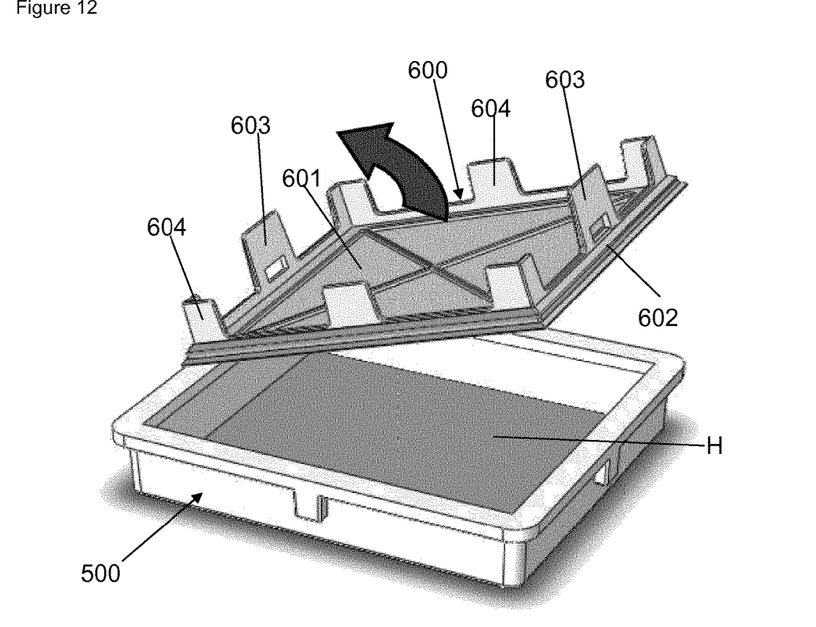
FIG. 12 shows a perspective view of the piston upon lifting it from the hydrogel layer in the graft frame.

Than one has the piston 600 released from the second component 400, which piston 600 usually sticks to the hydrogel layer H in the graft frame 500. The piston 600 is then manually lifted from the graft frame 500 as shown in FIG. 12.

According to an embodiment of the present invention, the membrane bottom 501 inside the graft frame 500 as well as said contact surface 601a of the piston 600 each comprise an area of 6 cm×7 cm. Other sizes are also possible. Thus the final compressed hydrogel layer comprises a corresponding area of e.g. 6 cm×7 cm and a thickness defined by screws 410, see above.

Figure 13:
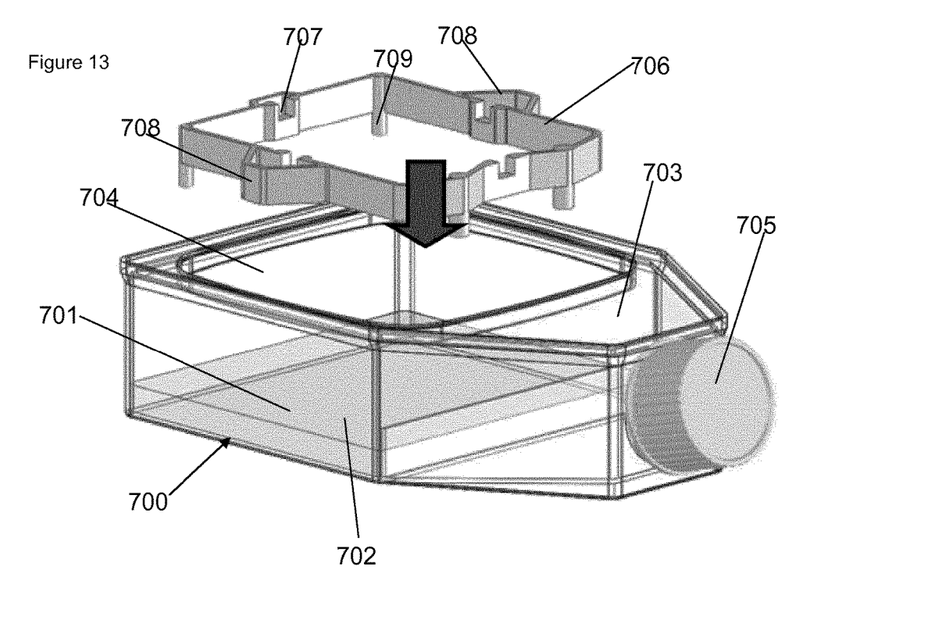
FIG. 13-16 shows perspective views of a flask for incubating the compressed hydrogel layer.
Figure 14:
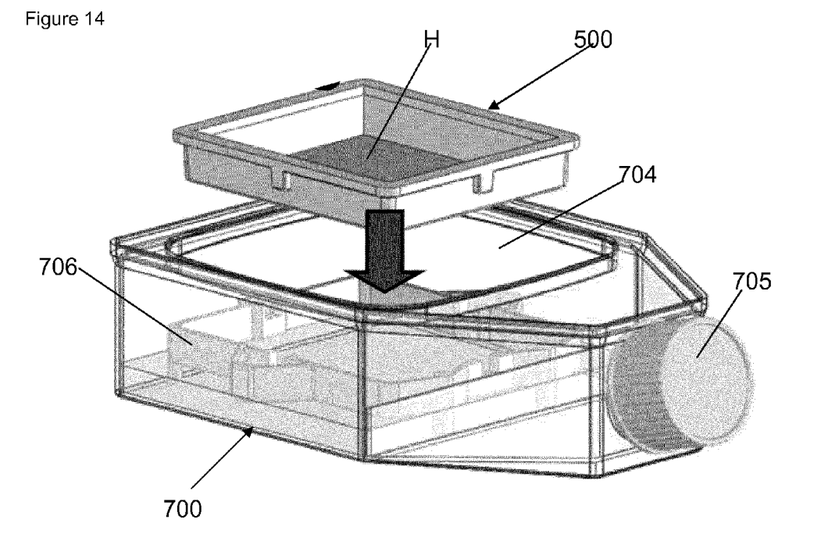
Figure 15:
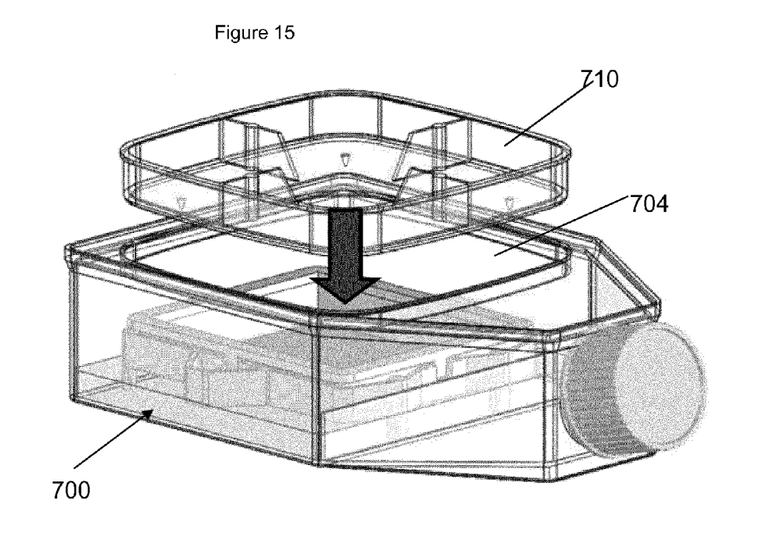
Figure 16:
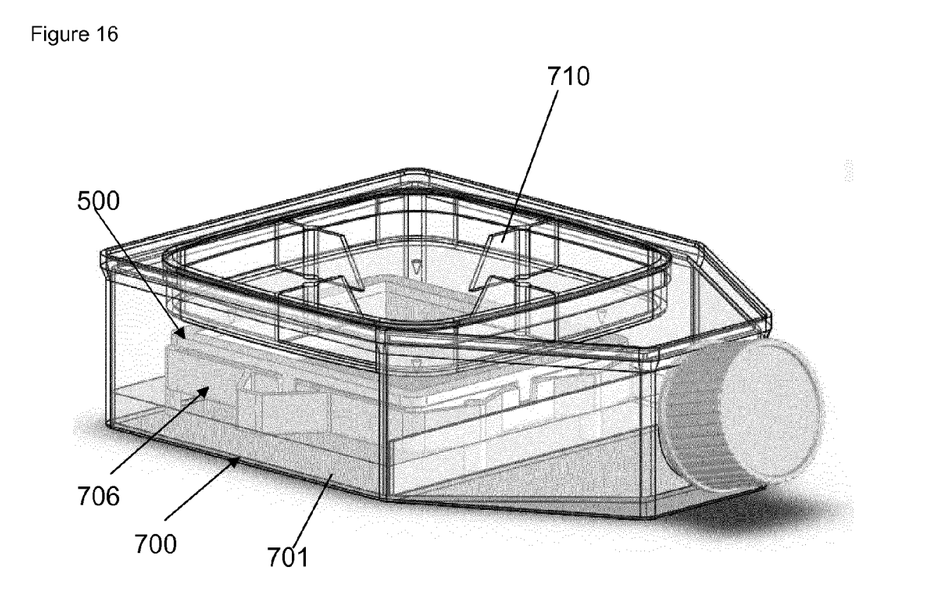

For further treatment of the compressed hydrogel layer H a flask 700 for incubation of the compressed hydrogel layer H is provided (cf. FIGS. 13 to 16). The flask 700 is designed to receive the graft frame 500 with the compressed hydrogel layer H residing in said graft frame 500. For this, the flask 700 comprises an opening 704 in a top part 703 of the flask 700 through which the graft frame 500 is arranged in an interior of the flask 700 as shown in FIG. 14. In beforehand, as shown in FIG. 13, a support frame 706 is arranged on a bottom 702 of the flask 700 through its opening 704 for supporting the graft frame 500. The support frame 706 comprises recesses 707 formed in an upper edge of the support frame 706 for receiving said portions 504 of the frame member 502 of the graft frame 500, wherein the graft frame 500 is designed to rest with its upper edge region 503 on said upper edge of the support frame 706. Particularly, the support frame 706 rests with four stands 709 on said bottom. Furthermore, the support frame 706 comprises two opposing protruding regions 708 for contacting a wall 702 of the flask 700 from the interior of the flask 700 so that the support frame 706 cannot be displaced inside the flask 700 in a lateral direction (cf. FIGS. 14 and 15).

Once the graft frame 500 is properly positioned in the support frame 706 inside the flask 700, the opening 704 of the flask is closed by means of a lid 710 which then presses the graft frame into the support frame 706 so that the graft frame is fixed along in a direction perpendicular to bottom 701 of the flask between the lid 710 and the support frame 706. It is also possible to arrange an additional element between said lid 710 and the graft frame 500 in order to press the graft frame against the support frame 706 by means of the lid 710.

Through a further opening that can be closed by a screw cap, a cell culture medium can be filled into the flask. The cell culture medium is required for both, the culture of the cells in and on the hydrogel layer, and for transportation of the dermo-epidermal grafts made from the hydrogel layer.

Preferably, the guiding frame 100 is made out of a stainless steel.

Further, the first component 200 is preferably made out of PEEK (Polyether ether ketone).

Further, the second component 400 is preferably made out of PEEK (Polyether ether ketone).

Further, the membrane bottom 501 of the graft frame 500 is preferably made out of PET (e.g. according to ISO 13485).

Furthermore, the piston 600 is preferably made out of Polypropylene.

REFERENCES

[1] Diezi, Mirco, Determining the conditions that regulate epidermal stratification in vitro: Engineering an epidermal substitute in 3 steps, Master Thesis in Human Biology, Tissue Biology Research Unit, University of Zürich, February 2009;

[2] Baroli, B., Hydrogels for tissue engineering and delivery of tissue-inducing substances. J Pharm Sci, 2007. 96(9): p. 2197-223.

[3] Mimura, T., et al., Tissue engineering of corneal stroma with rabbit fibroblast precursors and gelatin hydrogels. Mol Vis, 2008. 14: p. 1819-28.

[4] Stark, H. J., et al., Organotypic keratinocyte cocultures in defined medium with regular epidermal morphogenesis and differentiation. Journal of Investigative Dermatology, 1999. 112(5): p. 681-691.

[5] Yamaoka, H., et al., Cartilage tissue engineering using human auricular chondrocytes embedded in different hydrogel materials. J Biomed Mater Res A, 2006. 78(1): p. 1-11.

[6] Ferguson, R. E. and B. Rinker, The use of a hydrogel sealant on flexor tendon repairs to prevent adhesion formation. Ann Plast Surg, 2006. 56(1): p. 54-8.

The invention claimed is:

1. A device for compressing a hydrogel, comprising;
a graft frame (500) comprising a circumferential frame member (502) and a membrane bottom (501) connected to said frame member (502), wherein the graft frame (500) is designed to receive said hydrogel (H) so that a hydrogel layer (H) is formed covering said membrane bottom (501),
a guiding frame (100) having a plurality of guiding rods (104) extending along a compression direction (C),
a filter plate (300),
a base (201) having a plurality of openings (204), wherein each opening (204) is associated to one of the guiding rods (104), wherein the base (201) is designed to be arranged on the guiding frame (100) in an operating mode of the device such that each guiding rod (104) extends through its associated opening (204), wherein the device further comprises a circumferential wall (203) protruding from said base (201) to form a container (220) that is designed to receive the filter plate (300) and the graft frame (500) in said operating mode so that the filter plate (300) is arranged between a bottom (230) of said container (220) and the membrane bottom (501) of the graft frame (500),
a further base (401) having a plurality of openings (404), wherein each opening (404) is associated to one of the guiding rods (104), wherein the further base (401) is designed to be arranged on the base (201) in said operating mode, such that each guiding rod (104) that extends through its associated opening (204) of the base (201) is also inserted into its associated opening (404) of the further base (401) so that the further base (401) is guided by said rods (104) along the compression direction (C), a piston (600) that is designed to be connected to said further base (401) in a releasable manner in said operating mode of the device, wherein in said operating mode the further base (401) is designed to press the piston (600) along the compression direction (C) against said hydrogel layer (H) residing on the membrane bottom (501) of the graft frame (500) so as to compress the hydrogel layer (H) between the piston (600) and the membrane bottom (501).

2. The device according to claim 1, wherein the graft frame (500) and/or the piston (600) are designed as single-use items.

3. The device according to claim 1, wherein the piston (600) comprises a piston base (601) having a first side (601a) forming a contact surface for pressing against the hydrogel layer (H), wherein the piston (600) is designed to be inserted into the graft frame (500) with its contact surface (601a) ahead when pressing with its contact surface (601a) against the hydrogel layer (H), wherein the piston base (601) comprises a circumferential edge region (602) being designed to contact the frame member (502) of the graft frame (500) when pressing against the hydrogel layer (H).

4. The device according to claim 1, wherein the piston (600) comprises two latching elements (603) protruding from said edge region (602) of the piston base (601) on a second side (601b) of the piston base (601) facing away from said first side (601a) forming said contact surface.

5. The device according to claim 1, wherein the device comprises a support (402) for the piston (600), which support (402) protrudes from a first side (401a) of the further base (401) towards the membrane bottom (501) in said operating mode of the device, wherein the latching elements (603) are designed to engage with said support (402) for releasably connecting the piston (600) to the support (402).

6. The device according to claims 4, wherein the further base (401) comprises an aperture (420) for each latching element (603), through which the respective latching element (603) is accessible from a second side (401b) of the further base (401) facing away from said first side (401a) of the further base (401), so that the latching elements (603) can be released from the support (402) manually via said apertures (420).

7. The device according to claim 1, wherein the piston (600) comprises guiding elements (604) protruding from said edge region (602) of the piston base (601) on said second side (601b) of the piston base (601) facing away from said contact surface (601a), which guiding elements (604) are designed to slide along said support (402) for guiding the piston (600) with respect to the support (402) upon engaging the latching elements (603) with the support (402).

8. The device according to claim 1, wherein the device comprises an adjusting means for adjusting a penetration depth of the piston (600) along the compression direction (C) into the graft frame (500), wherein said adjusting means comprises two screws (410) that are screwed in an internal thread formed in the first side (401a) of the further base (401) adjacent to the support (402), so that the heights of the screw heads of said screws (410) with respect to said first side (401a) of the further base (401) can be adjusted by turning the respective screw (410) clockwise or counter-clockwise, wherein the screw heads (410) are designed to rest on said frame member (502) in the operating mode of the device so as to limit said penetration depth.

9. The device according to claim 1, wherein the further base (401) of comprises a receptacle (430) for receiving at least one weight element (800), so as to adjust the weight of the further base (401), by means of which the further base (401) compresses said hydrogel layer (H) in said operating mode of the device, wherein said receptacle (430) is formed by said support (402), wherein said receptacle (430) comprises an opening on the second side (401b) of the base (401), via which opening said at least one weight element (800) can be arranged in said receptacle (430).

10. The device according to claim 1, wherein said circumferential wall (203) of the container (220) comprises a step (205) for supporting said filter plate (300).

11. The device according to claim 1, wherein said graft frame (500) is designed to rest with a circumferential edge region (503) of the frame member (502) on an upper edge (206) of the wall (203) of the container (220) in said operating mode of the device, wherein said upper edge (206) of the wall (203) comprises at least one recess (207) for receiving a region (504) of the frame member (502) of the graft frame (500) in a form-fitting manner.

12. The device according to claim 1, wherein said wall (203) comprises a bulge (208) for taking the filter plate (300) and/or the graft frame (500) out of the container (220).

13. A system comprising a device according to claim 1, wherein the system further comprises a flask (700) for incubation of the compressed hydrogel layer (H), wherein said flask (700) is designed to receive the graft frame (500) with the compressed hydrogel layer (H) residing in said graft frame (500).

14. The system according to claim 13, wherein the flask (700) comprises an opening (704) through which the graft frame (500) can be arranged in an interior of the flask (700), wherein the flask (700) comprises a lid (710) for closing said opening (704), wherein said system comprises a support frame (706) being designed to be arranged in said interior of the flask (700) on a bottom (701) of the flask (700) and to support the graft frame (500), wherein the lid (710) is designed to press the graft frame (500) against the support frame (706) when the lid (710) closes said opening (704) of the flask (700), and wherein the flask (700) comprises a further opening for filling a liquid into the flask (700), and wherein a screw cap (705) is provided for closing said further opening, and wherein said flask (700) is transparent at least in sections, and wherein said flask (700) and/or the support frame (706) are designed as single-use items.

15. A method for compressing a hydrogel layer using a device according to claim 1, comprising the steps of:
    filling a hydrogel (H) into the graft frame (500) so that said hydrogel (H) forms a hydrogel layer (H) covering said membrane bottom (501),
    arranging the filter plate (300) in said container (220),
    arranging said graft frame (500) comprising the hydrogel layer (H) in said container (220) on top of the filter plate (300),
    arranging the base (201) on the guiding frame (100) so that the guiding rods (104) extend through their respective opening (204) of the base (201),
    arranging the further base 401 on the base (201) so that said guiding rods (104) are inserted into their respective opening (404) of the further base (401), and
    compressing the hydrogel layer (H) between the membrane bottom (501) and the piston (600) connected to the further base (401) by letting the further base (401) press with the piston (600) along the compression direction (C) against the hydrogel layer (H), wherein the further base (401) is guided by said guiding rods (104) along the compression direction (C).

16. The method according to claim 15, further comprising the steps of:

removing the graft frame (500) from the base (201) and the further base (401) after having compressed the hydrogel layer (H), arranging the graft frame (500) with the compressed hydrogel layer (H) through an opening (704) of a flask (700) in an interior of said flask (700) on top of a support frame (706) arranged on a bottom (701) of the flask (700), closing the opening (704) of the flask (700) with a lid (710), thereby pressing the frame member (502) of the graft frame (500) with the lid (710) against the support frame (706), so as to secure the graft frame (500) in the flask (700), and filling a cell culture medium into the flask (700), incubating the compressed hydrogel layer (H), adding keratinocytes to an upper surface of the hydrogel layer (H), which upper surface faces away from the membrane bottom (501).

\* \* \* \* \*